United States Patent [19]
Davloor et al.

[11] Patent Number: 5,113,711
[45] Date of Patent: May 19, 1992

[54] LIQUID SAMPLING DEVICE

[76] Inventors: Ramana Davloor, 295 Market Street, Port Elgin, Ontario, N0H 2C0, Canada; Richard Root, R.R. #4,, Paisley, Ontario N0G 2N0, Canada; Douglas R. Root, 9 Prince Albert Street, Delaware, Ontario, N0L 1E0, Canada

[21] Appl. No.: 495,485

[22] Filed: Mar. 19, 1990

[30] Foreign Application Priority Data

Apr. 4, 1989 [CA] Canada .................................. 595,605

[51] Int. Cl.$^5$ ............................................. G01N 1/12
[52] U.S. Cl. ....................................................... 73/864.63
[58] Field of Search ............ 73/864.63, 864.66, 864.65

[56] References Cited

U.S. PATENT DOCUMENTS

| | | | |
|---|---|---|---|
| 397,961 | 2/1989 | Bergmann | 73/864.63 |
| 1,210,487 | 1/1917 | Kaul | 73/864.63 |
| 1,526,104 | 2/1925 | Tuley | 73/864.63 |
| 1,603,712 | 10/1926 | Peck | 73/864.63 |
| 1,857,537 | 5/1932 | Frank et al. | 73/864.63 |
| 2,302,884 | 11/1942 | O'Neill | 73/864.66 |
| 2,554,832 | 5/1951 | Kulp | 73/864.66 X |
| 2,678,563 | 5/1954 | Parrish | 73/864.65 |
| 3,968,696 | 7/1976 | Rosenblum | 73/864.63 |
| 4,590,810 | 5/1986 | Hunkin et al. | 73/864.63 |
| 4,594,905 | 6/1986 | Roberts | 73/864.63 |

FOREIGN PATENT DOCUMENTS

| | | | |
|---|---|---|---|
| 174036 | 8/1965 | U.S.S.R. | 73/864.66 |
| 580478 | 11/1977 | U.S.S.R. | 73/864.63 |
| 593106 | 2/1978 | U.S.S.R. | 73/864.63 |
| 892264 | 12/1981 | U.S.S.R. | 73/864.66 |

*Primary Examiner*—Tom Noland
*Attorney, Agent, or Firm*—Stevens, Davis, Miller & Mosher

[57] ABSTRACT

A liquid sampling device is disclosed which is particularly suitable for sampling chemical wastes or hazardous chemicals. The device has a low resistance to flow so that composite samples can be obtained from a singal draw. A representative sample can be obtained of a liquid in a container throughout its depth, as opposed to taking several samples at various depths. The possibility of cross-contamination, when taking samples from several containers, is reduced as a result of fewer internal components and simplified replacement of contaminated parts. The overall structure, particularly that of the container for receiving and holding the sample, is simplified to make its production cost low enough for a disposable arrangement.

3 Claims, 4 Drawing Sheets

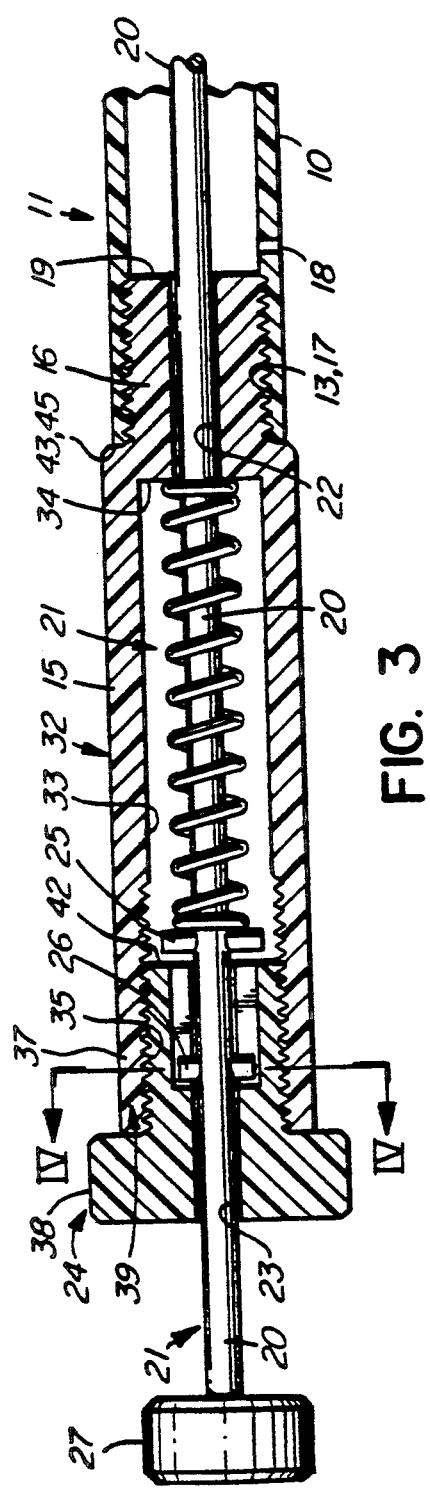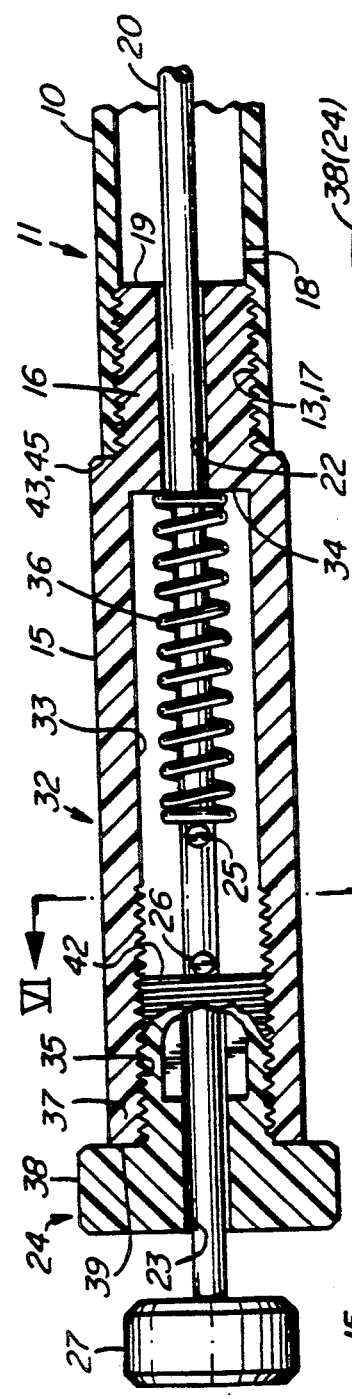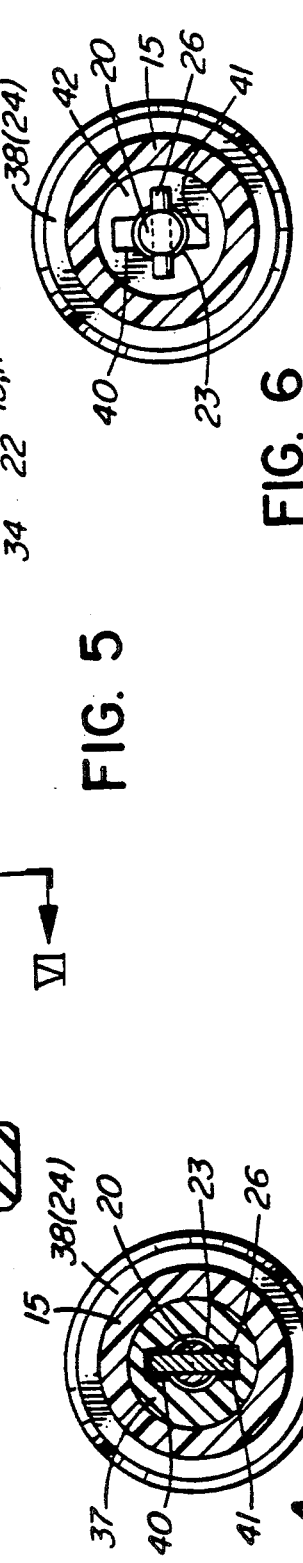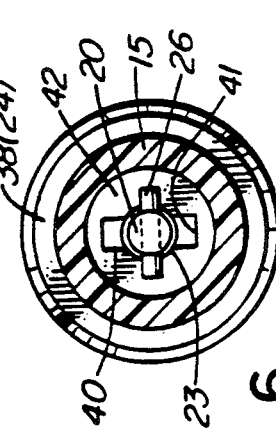

LIQUID SAMPLING DEVICE

BACKGROUND OF THE INVENTION

The present invention relates to liquid sample taking devices of the type provided with an elongated, usually tubular container portion which is provided at its normally lower end with a closing plug mounted at the end of a rod passing through the container and manipulated from the exterior of the container at the other, normally upper, end of the container.

A device of the above kind is typically used to take samples of hazardous chemicals. It is important that the device meet several prerequisites. It should be capable of withdrawing from the body of liquid to be sampled a composite sample, i.e. a sample which corresponds as closely as possible to the arrangement of the sampled body. The device should be capable of minimizing cross-contamination which could adversely affect the sample composition, hence sample results. In other words, it must be capable of quick and easy cleaning of its parts which come into contact with the sampled matter, or inexpensive enough to economically allow the disposal of its parts coming into contact with the sampled liquid. That is to say, at least those parts which are to come into contact with the sampled liquid should be as inexpensive as possible. Another desired feature is the possibility of an easy, quick and reliable assembling and disassembling of the parts contacting the liquid with or from the rest of the device so that the release can be more compatible with the liquid being sampled.

Many attempts have been made to provide a liquid sampling device as mentioned above, which would meet many of the above requirements. For instance, U.S. Pat. No. 1,603,712 issued Oct. 19, 1926 (Peck) discloses a sampling device used in measuring quantities of oil. The quantity determination is corrected for a temperature factor, and the device is designed to take, at any depth of a container, an amount of liquid proportional to the cross-sectional area of the container at that depth. When viewed from the standpoint of the present invention, the device is not only expensive to produce and cumbersome to operate but also fails to provide a smooth passage for the sampled liquid. Another device, U.S. Pat. No. 1,857,537 issued May 10, 1932 (Frank et al.) is disadvantageous as it requires a guiding bracket within the sample retaining container. Any sample flowing into the container from the bottom end must be disturbed by this obstruction. Besides, the mechanism for holding the closing plug sealingly against the container utilizes a camming surface engaged by a pin in the plunger rod. This mechanism may fail to provide good sealing engagement in one extreme, or may subject the plug to unnecessary compression causing premature wear of the closure member in the opposite extreme. U.S. Pat. No. 2,302,884 issued Nov. 24, 1942 (O'Neill) discloses a transparent oil level indicator which is allowed to rest at the bottom of an oil case while oil flows into its lower end. The lower end is closed by exerting pressure on the upper end of the casing. As in the preceding example, the inside of the container section is provided with a plurality of protrusions providing guide for the rod operating the cover at the bottom of the container. U.S. Pat. No. 2,554,832, issued May 29, 1951 (Kulp) presents another complex structure expensive to produce and thus not suitable for discarding, or difficult to maintain clean and thus prone to causing cross-contamination. The device is described as being suitable for determining temperature of stored liquids, and also being used in sampling at a selected elevation. Finally, reference may be had to U.S. Pat. No. 4,594,905, issued Jun. 17, 1986 (Roberts) and showing a somewhat complex liquid analyzer which also allows for sampling at a selected elevation, and includes a temperature indicating unit, among other things. This patent contains reference supporting the statement in the introduction of this description, namely that the field of sampling devices of this type is crowded.

In summary, the prior art of which the above references are believed to be most relevant, does not meet many of the above requirements. The closure activating mechanism parts, such as guide rings and travel stops are likely to interfere with fluid flow into the tubular element. If a non-homogeneous mixture was to be sampled, the flow rate of each component of the mixture into the tube would vary according to its physical properties (density, viscosity, etc.). A composite sample, from a drum for example, could not be obtained from a single draw, when using the prior art devices. This is why the prior art devices are useful only for taking samples at predetermined depths. The likelihood of cross-contamination increases when there are more internal parts that come into contact with the fluid being sampled. Most prior art devices have complicated internal structures.

To be useful as composite samplers for hazardous chemicals, the prior art devices would have to be used to take several samples from one container, at different depths. These samples would then have to be combined to provide a composite sample. The prior art samplers would have to be cleaned after each of these draws. To take several samples of waste from the same container, using a complicated decontamination procedure between samples, would be impractical. The procedure, if used for sampling hazardous chemicals, would likely be too tedious or dangerous to be practical. If the rod guides of, say, U.S. Pat. No. 1,857,537 were moved closer to the activating mechanism, i.e. away from the closure element, lateral stability of the rod would likely be reduced giving rise to difficulties with proper sealing of the closure member.

Components of the closure activating mechanism of the liquid samplers of the prior art are physically connected to the tubular elements of these devices. This construction makes it difficult to adapt the material of which the samplers components are made to the chemicals to be sampled. It is impossible for one sampler alone to be compatible with sufficiently many different chemical classes. Either several samplers made of different materials would have to be kept handy when using prior art configurations, or all incompatible components of the one sampler would have to be changed after each sample is taken.

SUMMARY OF THE INVENTION

It is an object of the present invention to alleviate the problems associated with prior art samplers and to further advance the art of the devices of this type.

In general terms, the invention provides a liquid sample taking device comprising, in combination: an elongated, hollow cylindric body having a first end and a second end; manipulating means removably secured to said first end of the body; a control rod having a first end portion slidably received in a portion of said manipulating means, an intermediate portion freely disposed within said body, and a second end portion freely disposed at the second end of the body, the rod being mounted in said manipulating means to allow reciprocating movement of said intermediate portion within said body generally coaxially therewith; a closure member secured to said rod at the second end thereof and being adapted to sealingly engage said second end of the body to close the body when the device is in a closed state and to be remote from the second end of the body, leaving the second end open, when the device is in an open state; vent means at the first end of the body, said vent means communicating the interior of the body with the atmosphere surrounding the device to allow the flow of a liquid into the body from the second end, when the body is held in a generally vertical position and partly submerged into a body of liquid to be sampled; the inner wall of said body being a smooth cylindric wall devoid of protrusions throughout the entire length of the body between said second end and said vent means; said control rod manipulating means including spring means operatively associated with the control rod to constantly urge same in a generally axial direction from the second end to the first end of the body and to maintain the rod in generally stationary relative said body; said manipulating means further including selectively releasable lock means operatively associated with said rod and with said spring means to block, when the device is in said open state, the movement of the rod in said direction, in which open state the closing member is remote from the second end of the body, and to release the blocking of the rod to allow its movement, under the force of said spring means, in said direction, to bring the closure member into sealing contact with the second end of the body to provide a closed state of the device.

BRIEF DESCRIPTION OF THE DRAWINGS

The invention will now be described by way of a preferred embodiment with reference to the accompanying diagrammatic, simplified, out-of-scale drawings, wherein:

FIG. 3 is a longitudinal section III—III of FIG. 1;

FIG. 4 is section IV—IV of FIG. 3;

FIG. 5 is longitudinal section V—V of FIG. 2;

FIG. 6 is section VI—VI of FIG. 5;

DETAILED DESCRIPTION OF A PREFERRED EMBODIMENT

Figure 7:
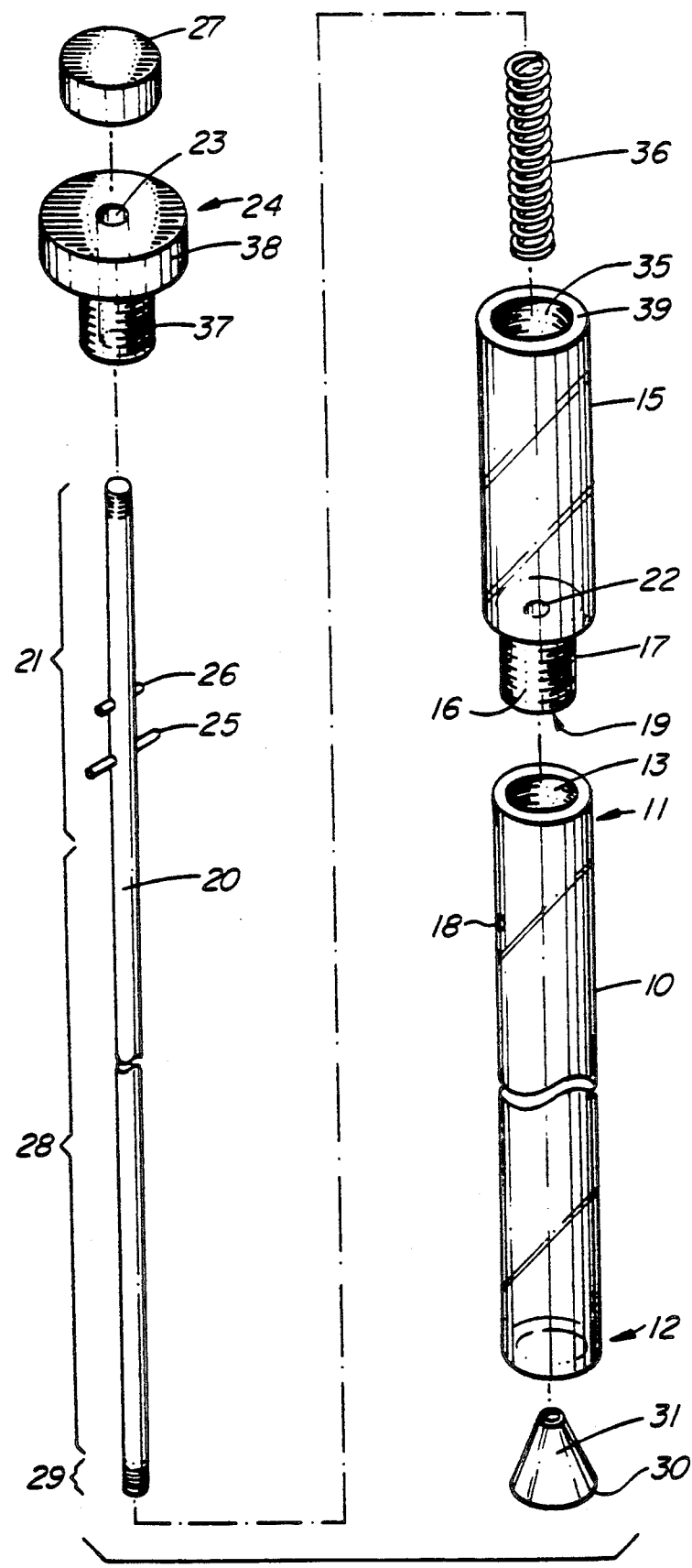
FIG. 7 is an exploded view of the device showing how the individual components of the device are secured to each other.

Referring first to FIG. 7, reference numeral 10 denotes an elongated, hollow cylindric container or body. The body 10 has a first end 11 and a second end 12. The body 10 is made from suitable material, in the embodiment shown, from transparent polyacrylic. Of course, the body could also be made from a variety of other materials including polyvinyl chloride (PVC) or from cardboard with polyethylene lining on both sides. The first end 12 of the body 10 is provided with an internal thread 13 the size and depth of which is contiguous with the size and thickness of the body 10. The body 10 of the embodiment shown has the length of about 4 ft. Its inside diameter is 1 inch and the thickness of the cylindric wall 10 is about ⅜". The thread 13 is a ⅞14 thread and is tapped over a length of about 1".

Figure 1:
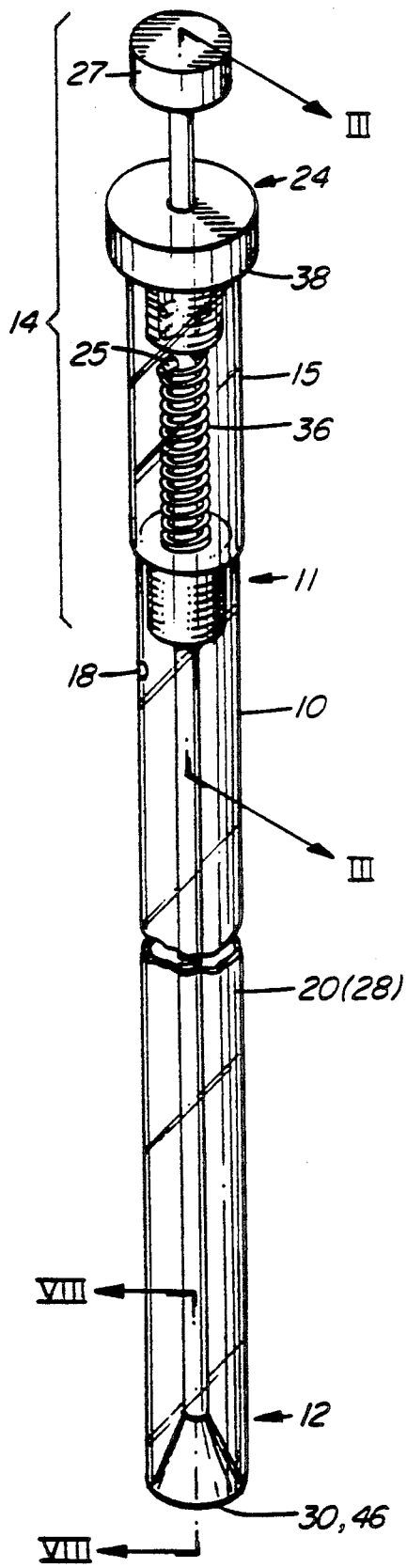
FIG. 1 is a perspective view, partly broken away, of the preferred embodiment, with certain parts simplified or omitted for the sake of clarity, the device being shown in closed state.

Reference numeral 14 (FIGS. 1 and 2) denotes a part of the device which is summarily referred to as "manipulating means" for reasons which will become apparent as the description proceeds. It can be seen from FIGS. 3 and 5 that the main portion of the manipulating means presents the configuration of a sleeve 15 which is provided, at one end thereof, with a reduced diameter portion 16. The reduced diameter portion 16 of the sleeve 15 is integral with a major diameter portion 32 which is of an outside diameter generally equal to the outside diameter of the body. An outer shoulder 45 is formed at the transition between the major diameter portion 32 and the reduced diameter portion 16 of the sleeve 15. The surface of the reduced diameter portion is threaded at 17 by a thread compatible with the thread 13 of the body 10. When the two threads 13, 17 are fully joined, the flat end face 43 at the first end 11 of the body 10 abuts against the outer shoulder 45 of the manipulating means 14. The thread 17 serves the purpose of removably securing the entire manipulating means 14 to the body 10 so that the body 10 can be removed for cleaning or replacement A vent 18 in the body 10 is spaced just inside the body 10, close to the normally lower face 19 of the sleeve 15. The vent is above the maximum liquid level in the container. The vent allows for atmospheric conditions inside the body 10 so that the liquid to be sampled can flow into the body 10 without a pressure buildup inside the device.

Figure 8:
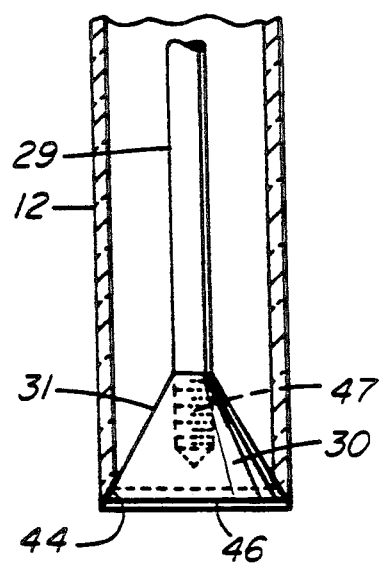
FIG. 8 is a detail, in a perspective view, of the lowermost part of the device, showing the closure member in a closed state.

The angled end face 44 at the second end 12 of the body 10 is tapered with an angle, in the embodiment shown, of 30 degrees from the horizontal, as is shown in FIG. 8. The angle matches that of the closure member so that a tight seal can be provided over the area of contact without the need to use a sealing member such as a gasket, between the contacting parts. It is to be observed that the inside wall of the cylindric body is smooth throughout the entire length thereof, except for the threaded portion 13 at the first end 11 of the body 10. Thus, when the device is assembled as in FIG. 1 or FIG. 2, there is no protrusion or rough surface part at the inside of the cylindric wall of the body 10, all the way from the second end 12 to the vent 18.

A control rod 20 passes through the body 10 and through the sleeve 15. For the purpose of this description, three portions of the rod are described even though the rod is an integral, cylindric piece having, in the embodiment shown, a ¼ in. diameter over generally the entire length. One part of the first end portion 21 of the rod 20 is slidable in a passage 22 in the small diameter portion 16 of the sleeve 15. Another part of the first end portion 21 is slidably received in a passage 23 provided in a cylindric cap 24 which forms, in assembled state, a part of the manipulating means 14. In the embodiment shown, the first end portion is further provided with two dowels 25, 26 disposed at an axial spacing from each other and with a control member of the type of a knob 27.

An intermediate portion 28 of the rod 20 is that part which is disposed within the body 10 when the device is in an assembled state. The normally lower end of the rod 20 is designated as a second end portion 29 of the rod 20.

Figure 9:
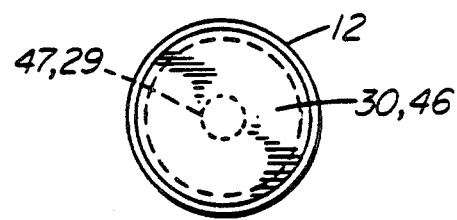
FIG. 9 is a bottom view of the representation in FIG. 8.

A closure member 30 is threaded on the second end of the rod 20 at the closure member internal thread 47. The conical closure member is a resilient plug having a frustoconical surface portion 31. The smallest diameter of the closure member 30 is approximately equal to the diameter of the control rod 20, while the major diameter is slightly less than the outside diameter of the body 10 but larger than the inside diameter of the same. Refer to FIG. 9. When the device is in the closed state, the smooth surface of the closure member 30 and the clearance between the second end of the body 12 and the closure member 30 allows for free flow of liquid into the body 10 with little resistance so that a representative sample of liquid can be taken. The closure member 30 has an angle that matches the angled end face 43 of the second end of the body 12. This is shown in FIG. 8. When the device is in the closed state, a tight seal is achieved over the surface area covered by the angled end face 43. In this way, a seal is provided without using a sealing member such as a gasket between the contacting parts. The flat end surface 46 of the closure member 30 lines up with the edge of the second end 12 of the body 10 when the device is in the closed state, thereby letting the device capture a sample at the very bottom of the container. That is, when the device is closed and touching the bottom of the container, the second end of the body 12 will not be raised above the inside bottom surface of the container. The closure member 30 is removably secured to the second end of the body 12 so that the device parts can be disassembled for cleaning or replacement. The internal thread 47 of the closure member 30 starts at the smallest diameter to approximately two-thirds of the way through the axis of the closure member 30. Referring to the closure member 30, the conical shape was chosen because it was found that the closure member 30 reseats well at the angled end face 43.

Reference should now be had to FIGS. 3 to 6 which show the arrangement of the manipulating means 14. Most of the major diameter portion 32 is hollow to provide a cylindric cavity 33 the diameter of which is substantially greater than that of the passage 22. Accordingly, a shoulder 34 is formed at the point of transition between the passage 22 and cavity 33. The end of the sleeve 15 remote from the reduced diameter portion 16 is provided with an inner thread 35 made in the wall of the cavity 33.

As seen from FIGS. 3 and 5, the cavity 33 houses a compression coil spring 36 whose one end engages the dowel 25, also referred to as a boss, while the other end abuts against the shoulder 34. The dowel 25 must have a length longer than the outside diameter of the spring 36 so that the dowel 25 does not get caught inside the spring 36 when the rod 20 moves to bring the device in the open or closed state. The arrangement of the spring 36 and the dowel 25 is such that the spring is under constant compression thus constantly subjecting the rod 20 to a force in the direction from the second end 12 of the body 10 to the first end 11 thereof, regardless whether the instant state of the closure member 30 is open or closed. Therefore, when the device is in the closed state, spring tension ensures that a tight seal is maintained between the closure member 30 and the second end 12 of the body 10. When the device is in the open state, spring tension ensures that the rod 20 assists the passages 22, 23 in maintaining the rod 20 in the generally axial position. Additional explanation follows in the description of the releasable lock mechanism.

Referring to FIGS. 3, 5 and 7, the thread 35 is compatible with and receives the threaded portion 37 of the cap 24 which, in the embodiment shown, is integral with a cylindric head section 38 abutting against the end 39 of the sleeve 15 opposite to the face 19. As mentioned above, there are two passages 22, 23, one—22—in the reduced diameter portion 16, the other—23—in the cap 24. Thus, the rod is maintained generally co-axial with the axis of the body 10 at two discrete, axially spaced apart points.

The manipulating means 14 also includes releasable lock means the preferred embodiment of which will now be described in detail with particular reference to FIGS. 3 to 6.

Figure 2:
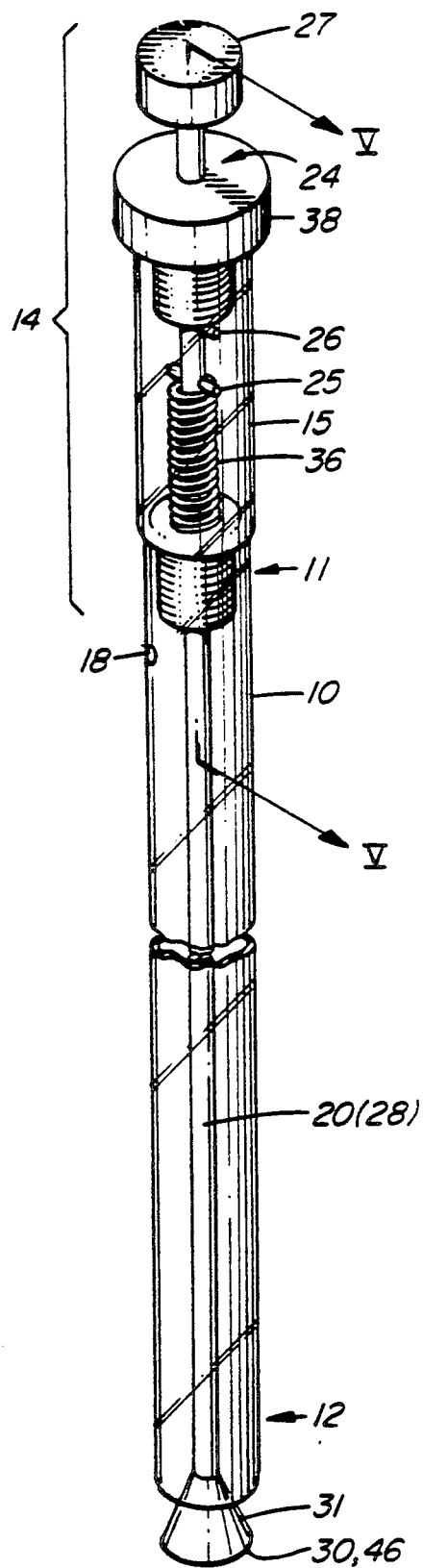
FIG. 2 is a perspective view similar to that of FIG. 1 but showing the device in open state.

As mentioned above, there are two dowels 25, 26 fixed to the first end portion 21 of the rod 20. The dowel 26 protrudes to each side of rod 20 a distance which is substantially greater than the radius of the passage 23 but is smaller than the radial depth of the respective one of the diametrically opposed slots 40, 41. The slots 40, 41 are adapted to accommodate the dowel 26, when it is aligned therewith. The pair of slots 40, 41 thus cooperates with the spring 36 and with the remaining parts of the manipulating means 14 to provide for a closed position, i.e. a position wherein the dowel 26 is aligned with and positioned in the slots 40, 41 and the closure member 30 engages the end 12, being urged to and maintained in the closed position by the action of the spring 36, and in an open position in which the rod 20 is pushed, by means of the knob 27, in a direction toward the second end of the body 10, i.e. against the action of the spring 36, to disengage the closure member 30 from the end 12 of body 10 and, eventually, to bring the dowel 26 out of the slots 40, 41. When the dowel 26 clears the slots 40, 41, the knob 27 can be turned and with it the entire rod 20, to bring the dowel 26 out of alignment with the slots 40, 41. Upon release of the knob 27, the dowel 26 rests on an inner face 42 of the threaded portion of the cap 24 locking the closure member 30 in an open state. This situation is shown in FIGS. 2, 5 and 6. It is noteworthy that in the open, locked position, the spring 36, pressing against the boss or dowel 25, causes the dowel 26 to firmly engage the face 42 of the cap 24 thus assisting in maintaining the rod 20 generally stationary relative to the body 10. It will be appreciated that without the action of spring 36, the rod 20 could jiggle (within the limits of free play in passages 22, 23) inside the body 10 thus disturbing the flow during sampling and creating resistance to same.

When the device is in the closed state, the dowel 26 rests along the length of the slots 40, 41. When the device is in the open state, the dowel 26 abuts against the face 42 of the cap 24. It is apparent that the distance the dowel 26 travels along the length of slots 40, 41 while going from its position when the device is in the closed state to its position when the device is in its open state determines the opening achieved between the closure member 30 and the angled end face 44 at the second end 12 of the body 10. In the embodiment shown, the dowel 26 travels approximately 1 inch. The clearance between the closure member 30 and the angled end face 44 can be changed by using a cap 24 with a longer or shorter threaded portion 37. The inner thread 35 oaf the sleeve 15 is longer than the threaded portion 37 of the cap 24 in the embodiment shown. The inner thread 35 can therefore accept a cap 24 with a threaded portion 37 that is equal in length to the inner thread 35. In order to ensure that the face 42 of the cap 24 is at the correct position inside the sleeve 15, the cap 24 is threaded over a length sufficient to assure safe abutting of the cylindrical head section 38 of the cap 24 against the end 39 of the sleeve 15.

Since user safety is an important factor during the process of sampling hazardous liquids, consideration has been given to making the device convenient, simple and safe to operate. The diameter of the major diameter portion 32 of the sleeve 15, in the embodiment shown, is approximately one-half inch greater than the outside diameter of the sleeve 15. The overall length of the major diameter portion 32 is about 4 inches. Also, the knob 276, in the embodiment shown, is approximately 2 inches from the cap 24 When the device is closed. Hence, the user can open and close the device by grasping with one hand the sleeve 15 and pressing the knob 27 with the thumb of the same hand. While withdrawing the liquid filled device from the container, the hand can rest against the cylindrical head section 38 of the cap 24 for support.

In operation, the device is held in a vertical position with the closure member 30 down. Assuming that the device is in the closed state of FIG. 1, the sampler is first brought to its open state shown in FIG. 2 by pushing the control knob 27 against the action of the spring 36 downward towards the head section 38. This forces the rod 20 downwardly and causes the dowel 26 to move down through the slots 40, 41 in the threaded portion 37 of the cap. The downward movement of the rod 20 causes the closure member 30 to be unseated from the second end 12 of the body 10. When the dowel 26 passes the face 42 of the threaded portion 37 of the cap 24, the control knob 27 is rotated about 45 degrees to take the dowel 26 out of alignment with the slots 40, 41. This actuation, combined with the continuously acting force of the spring 36, causes the dowel 26 to abut the face 42 and thus locks the liquid sampler in the open position. The closure member 30 will remain unseated even if the user stops applying pressure to the control knob 27.

The sampler is then lowered into the container which contains the liquid to be sampled. The slower the device is lowered into the container, the more representative the sample obtained. Since the closure member 30 is remote from the second end 12 of the body 10, the liquid flows freely into the body 10. Within the body 10, it continues to flow smoothly as there are no obstacles in its path, until it reaches the desired level which is below the level of the vent 18. After the fluid has entered the body 10 through its second end 12, which is now open, the control knob 27 is rotated to realign the dowel 26 and the slots 40, 41. The force exerted by the spring 36 in the open state causes the rod 20 and the dowel 26 to move upwardly through the slots 40, 41. The upward motion of the rod 20 relative to the body 10 causes the closure member 30 to be reseated in the second end 12 of the body 10. In practice, the closure member 30 rests on the bottom of the container from which the sample is to be taken and the entire assembly of the manipulating means and the body moves down towards closure member 30. In this way, a bottom sample is obtained. As mentioned above the force exerted by the spring 36 in the open state thus prevents jiggling movement of the rod which enables a good representative sample to be obtained. When the closure member 30 is closed, the spring 36 provides sufficient force to maintain a good seal between the closure member 30 and the body 10.

In order to withdraw the sampler from the liquid, the user holds the cap 24 of the device with one hand, raises the device sufficiently to grasp the body with a piece of absorbent material in the other hand. The body 10 is then slowly drawn from the liquid using the hold on cap 24. Liquid is removed from the external surface of the body 10 by the absorbent material. The sample contained in the device can now be emptied into a collection bottle by pushing the control knob 27 to unseat the closure member 30 from the second end 12 of the body 10.

If there are several containers of hazardous chemical to be sampled, or if waste has been segregated according to class, the following procedure would be appropriate for taking a sample from a second, or further container. The same procedure would also be appropriate for taking samples of hazardous chemicals if they are appropriately segregated.

A first sample is captured and discharged into a collecting bottle using the procedure previously outlined. Contamination should be minimal as the sample is drawn into the body 10. The residues of the first captured sample should be flushed from the body either into the container from which it was obtained (if cross-contamination is not of major concern) or into a separate container (if cross-contamination is of major concern). The flushed body or tube is then used to capture a second sample from the container. The initial flushing allows for a more representative sample to be taken.

If there are several containers of hazardous chemical to be sampled, and if the waste has not been segregated according to waste class, or if there are several containers of hazardous chemicals such that the possibility of cross-contamination causes significant concern, the following procedure is appropriate for taking a sample from a second or subsequent container. First, the closure member 30 and the body 10 that were used to take a sample from a first container are unscrewed and removed. Then the rod 20 is cleaned. Closure member 30 and body the body 10 are replaced by new or cleaned components made of materials appropriate for the liquid to be sampled. A sample can then be taken by following the procedure previously outlined.

Those skilled in the art will appreciate that the above description relates to a preferred embodiment which may be modified to a greater or lesser degree without departing from the scope of the present invention. Accordingly, we wish to protect by Letters Patent which may issue on this application all such embodiments as properly fall within the scope of our contribution to the art.

We claim:

1. Liquid sample taking device comprising, in combination:
   a) an elongated, hollow cylindric body having a first end and a second end;
   b) manipulating means removably secured to said first end of the body;
   c) a control rod having a first end portion slidably received in said manipulating means, an intermediate portion freely disposed within said body, and a second end portion freely disposed at the second end of the body, the rod being mounted in said manipulating means to allow reciprocating movement of said intermediate portion within said body generally coaxially therewith;

d) a closure member secured to said rod at the second end thereof and being adapted to sealingly engage said second end of the body to close the body when the device is in a closed state and to be remote from the second end of the body, leaving the second end open, when the device is in an open state;

e) vent means at the first end of the body, the vent means communicating the interior of the body with the atmosphere surrounding the device to allow the flow of a liquid into the body from the second end, when the body is held in a generally vertical position and partly submerged into a body of liquid to be sampled;

f) the inner wall of said body being a smooth cylindric wall devoid of protrusions throughout the entire length of the body between said second end and said vent means;

g) the control rod manipulating means including spring means operatively associated with the control rod to constantly urge the same in an axial direction from the second end to the first end of the body;

h) said manipulating means further including:
 i) selectively releasable lock means operatively associated with said rod and with said spring means, to block, when the device is in said open state, the movement of the rod in said direction, in which open state the closing member is remote from the second end of the body, and to release the blocking of the rod to allow its movement, under the force of said spring means, in said direction, to bring the closure member into sealing contact with the second end of the body to provide said closed state; and
 ii) a control member fixedly secured to the rod at the first end portion thereof, to allow selectable pushing of the rod to move the same through said manipulating means, against the action of said spring means, to open the lower end of the body, and to turn the rod about a central longitudinal axis thereof to bring the same from a released position to a position in which the movement of the rod is blocked to hold the closure member in an open state; and a rod guide member slidably engaged with the rod at said first end portion, said guide member being threadably secured to the first end of the body by a thread complementary with an inner thread provided at an inner surface of the first end of the body.

2. The device of claim 1, wherein the spring means is a compression spring abutting at one end thereof against an abutment surface of the guide member, said abutment surface facing away from the second end of the body, an opposite end of the spring being in abutment with a retainer member of said rod, the disposition of the compression spring, the abutment surface, the retainer member and the closure member being such that when the closure member sealingly engages the second end of the body to close the same, the spring is under compression sufficient to hold the closure member in a sealing engagement with the second end of the body.

3. The device of claim 2, wherein said lock means includes a boss protruding radially outwardly from the rod at a point near the first end thereof, said guide member including a hollow, generally cylindric passage in a sliding contact with a surface of the rod which is also generally cylindric, an axially elongated groove provided in said cylindric passage, the groove being aligned with the boss allowing movement of said boss along the passage as the rod is pushed against the action of the spring to open the second end of the body, said passage terminating at a locking surface facing toward the second end of the body and being so arranged and disposed that—on full opening of the lower end of the body—the boss is brought beyond the passage allowing the rod to be turned about its axis to bring the boss out of alignment with the groove, whereupon, following release of the push on the rod, the boss engages the locking surface preventing the displacement of the rod in the direction of force exerted by the spring.

* * * * *